United States Patent [19]

Stacpoole

[11] Patent Number: 4,558,050

[45] Date of Patent: Dec. 10, 1985

[54] TREATMENT OF METABOLIC DISORDERS WITH DICHLOROACETATE-THIAMINE PREPARATIONS

[75] Inventor: Peter W. Stacpoole, Gainesville, Fla.

[73] Assignee: University of Florida, Gainesville, Fla.

[21] Appl. No.: 584,994

[22] Filed: Mar. 1, 1984

[51] Int. Cl.$^4$ ................. A61K 31/505; C07D 239/02; C07D 415/00

[52] U.S. Cl. .................................... 514/252; 544/327

[58] Field of Search ....................... 544/327; 424/251; 514/252

[56] References Cited

PUBLICATIONS

Jacob Gutman, Modern Drug Encyclopedia and Therapeutic Guide, 1941.

Primary Examiner—Donald G. Daus
Assistant Examiner—Cecilia Shen
Attorney, Agent, or Firm—Dennis P. Clarke

[57] ABSTRACT

Chemical compounds useful in the treatment of metabolic disorders comprising the reaction product of thiamine and a dichloroacetic acid.

30 Claims, No Drawings

TREATMENT OF METABOLIC DISORDERS WITH DICHLOROACETATE-THIAMINE PREPARATIONS

BACKGROUND OF INVENTION

1. Field of Invention

The present invention relates to novel compounds and compositions, useful for the treatment of certain metabolic diseases.

2. Prior Art

The pharmacologic and therapeutic properties of salts of dichloroacetec acid (DCA) have been extensively studied over the last several years. Researchers have found that DCA stimulates glucose uptake and utilization by peripheral tissues [Stacpoole et al., Metabolism, 19:71 (1970); McAllister et al., Biochem. J. 134:1067 (1973); Diamond et al., Diabetes 31:326 (1982)] and inhibits hepatic glucose production [Stacpoole, Metabolism26:107 (1977); Demangre et al., Biochem. J. 172:91 (1978); Diamond et al., Metabolism 30:880 (1981)]. It has also been found to decrease blood glucose levels in patients with diabetes mellitus [Stacpoole et al., N. Eng. J. Med. 298:526 (1978)]. DCA also stimulates lactic acid oxidation in animal tissues and significantly decreases lactic acid levels and overall morbidity in patients with lactic acidosis [Stacpoole et al., N. Eng. J. Med 309:390 (1983); Blackshear et al., Diabetes Care 5:391 (1982)]. In addition, DCA reduces circulating triglyceride and cholesterol concentrations in obese [Felts et al., Diabetes, 25 (suppl):363 (1976)] and diabetic [Hayek et al., Metabolism 29:120 (1980); Riles et al., Diabetes 28:852 (1979) animals. DCA also markedly decreases blood cholesterol levels in patients with various forms of hyperlipidemia [Stacpoole et al., N. Eng. J. Med. 298:526 (1978); Moore et al., Atherosclerosis 33:285 (1979)].

The efficacy of DCA for the treatment of metabolic disorders, however, is compromised by the fact that DCA is toxic to lower animals and humans, particularly upon chromic administration. It has been reported that a human patient who received DCA for about four months developed a mild polyneuropathy that resolved when treatment stopped [Moore et al., ibid.]. Chronic administration of DCA to lower animals in doses exceeding those used clinically also induces a reversible peripheral neuropathy, changes in testicular morphology and lenticular opacities [Stacpoole, N. Eng. J. Med. 300:372 (1979)].

DCA is known to oxidize in vivo to glyoxylate and subsequently to oxalate [Demangre et al., Biochem. Biophys. Res. Comm. 85:1180 (1978); Harris et al., Arch. Biochem. Biophys. 189:364 (1978)]. Oxalate is known to cause neurotoxicy [Bilbao et al., Can. J. Neurol. Sci. 3:63 (1976)] and lenticular opacities [Fielder et al., Br. J. Ophthal. 64:782 (1980)], and may be at least partly responsible for the toxic effects associated with the chronic administration of DCA.

It is an object of the present invention to ameliorate the toxicity associated with DCA and provide compounds, compositions and methods for safe and effective treatment of certain metabolic disorders.

SUMMARY OF THE INVENTION

The present invention provides a novel chemical compound prepared by reacting thiamine or a pharmaceutically active derivative thereof, e.g., a thiamine metabolite and dichloroacetic acid.

The present invention also provides a method for preparing the above-described compound comprising reacting dichloroacetic acid or a reactive derivative thereof with thiamine and recovering the reaction product.

The present invention also provides a pharmaceutical composition in unit dosage form adapted for administration to a lower animal or human for the treatment of a metabolic disease comprising a therapeutically effective amount of (1) the above-described compound or anion salt of a pharmaceutically acceptable cation and dichloroacetic acid and (2) an amount of thiamine or a pharmaceutically active derivative thereof sufficient to reduce the toxicity to the lower animal or human of the compound or salt of dichloroacetic acid.

There is also provided by the present invention a method for the treatment of a metabolic disease comprising the administration to a lower animal or human in need thereof a therapeutically effective amount of the above-described compound or a salt of a pharmaceutically acceptable cation and dichloroacetic acid and an amount of thiamine necessary to reduce the toxicity to the lower animal or human of the compound or the salt.

DETAILED DESCRIPTION OF THE INVENTION

Salts of dichloroacetic acid are referred to herein as "DCA" whereas free dichloroacetic acid is referred to as "acid".

It is known that the presence of DCA or acid in lower animals or humans stimulates the vitamin $B_1$-dependent enzymes, pyruvate dehydrogenase and alpha-ketoglutarate dehydrogenase. Thiamine is converted, in vivo, to an active metabolite such as thiamine pyrophosphate by ATP. The metabolites function in the body as enzyme cofactors. The present invention is predicated upon the hypothesis that the toxicity associated with chronic DCA or acid administration could be due to depletion of the body vitamin $B_1$ stores by the enhanced thiamine-dependent enzyme activities and to the toxin, oxalate, which accumulates in thiamine deficiency [Takasaki, Invest. Urol. 7:150 (1969)] and which is produced by metabolism of DCA. It was theorized that the toxicity of DCA or acid could be greatly diminished or eliminated by ensuring that thiamine levels in the body remain high when DCA is administered.

Thiamine or a pharmaceutically active derivative thereof may be administered according to the present invention (1) in the form of a compound produced by reaction thereof with dichloroacetic acid, (2) in the form of a mixture with the salt of dichloroacetic acid, or (3) prior to, subsequent to, or substantially simultaneously with the administration of DCA.

The pharmaceutical composition of the invention preferably contains a pharmaceutically acceptable carrier suitable for rendering the compound or mixture administrable orally as a tablet, capsule or pill, or parenterally or transdermally. The active ingredient may be admixed or compounded with any conventional, pharmaceutically acceptable carrier. It will be understood by those skilled in the art that any mode of administration, vehicle or carrier heretofore employed for the administration of DCA alone may be utilized for preparing and administering the pharmaceutical compositions of the present invention. Illustrative of such methods, vehicles and carriers are those described by Stacpoole et al. [N. Eng. J. Med., 309:390 (1983) and N. Eng. J. Med. 298:526 (1978)], the disclosures of which are incorporated herein by reference. Those skilled in the art, having been exposed to the principles of the invention will experience no difficulty in determining suitable and appropriate vehicles, excipients and carriers or in compounding the active ingredients therewith to form the pharmaceutical compositions of the invention.

Thiamine is capable of reacting with the acid to form either an ester, amide or salt-complex, depending upon the reaction conditions employed. The acid will also react with metabolites of thiamine, such as thiamine pyrophosphate, to form similar compounds. It will be understood that the present invention includes any pharmaceutically acceptable reaction product formed by reacting the acid or reactive derivative thereof with thiamine or any derivative thereof.

The therapeutically effective amount of DCA or acid/thiamine compound to be included in the pharmaceutical composition of the invention depends, in each case, upon several factors, e.g., the type, size and condition of the animal, the metabolic disorder to be treated, the intended mode of administration, the capacity of the animal to incorporated the intended dosage form, etc. Generally, an amount of DCA or acid/thiamine compound is included in each dosage form to provide an amount of DCA or acid employed in conventional pharmaceutical compositions containing DCA alone (Cf. Stacpoole et al., supra), i.e., from about 100 to about 10,000 mg, preferably from about 100 to about 5,000 mg.

The amount of thiamine to be included in the composition will depend upon the same factors noted above, and in particular, upon the degree of toxicity associated with the pressure of DCA or acid in the animal undergoing treatment. Generally, however, an amount of thiamine is included in the composition, either in admixture with DCA or as a compound with the acid or derivative thereof to provide a mass ratio of thiamine to DCA or acid of from about $1 \times 10^{-5}:1$ to about $10:1$, preferably from about $1 \times 10^{-3}:1$ to about $0.2:1$.

The DCA employed in the pharmaceutical compositions and methods of treatment of the invention may comprise the salt of dichloroacetic acid and any pharmaceutically acceptable cation, e.g., alkali metals such as sodium, potassium, lithium, alkaline earth metals such as magnesium, calcium, heavy metals such as manganese, iron, zinc, etc., and ammonium, etc. For the purpose of economy, availability and ease of formation and purification, however, it is preferred to employ an alkali metal salt, of the acid, most preferably the sodium salt.

The compound, compositions and method of the invention are useful for the treatment of a wide variety of metabolic disorders. Those skilled in the art will appreciate that the invention is applicable for the treatment of any disorder for which the administration of DCA has been found to be effective. Exemplary of such disorders are diabetes mellitus, hyperlipidemia (hypercholesterolemia, hypertriglycidemia, or both) and lactic acidosis.

The dichloroactic acid-thiamine compound or the mixture of DCA and thiamine may be solubilized in a suitable solvent, e.g., water, conventional physiological buffer solutions (phosphate, bicarbonate, lactate) or other medicinal solvents such as dimethyl sulfoxide, etc., and lyophilized for later reconstitution with the above-noted carrier media for parenteral, oral or transdermal administration.

The components of the composition of the invention may also be separately packaged in kit form, i.e., one package comprising the dichloroacetic acid-thiamine compound or DCA salt in unit dosage form, and the other package comprising thiamine or pharmaceutically active derivative thereof in unit dosage form. The respective dosages could be separately administered to the patient or combined before administration as a single dose.

Those skilled in the art will be aware that the amounts of the various components of the compositions of the invention to be administered in accordance with the method of the invention to a patient will depend upon those factors noted above.

Generally, however, amounts of DCA or acid/thiamine compound are administered to provide dosages of DCA or acid conventionally employed in the treatment of metabolic disorders, i.e., from about 1 to about 100 mg/kg, preferably from about 10 to about 50 mg/kg, the frequency of administration and duration of treatment being dependent upon the type and nature of the animal and metabolic disorder treated.

The amount of thiamine or pharmaceutically active derivative thereof co-administered with the acid component, either in admixture or in the form of a reaction product therewith is that necessary to provide the mass ratios of thiamine to DCA or acid set forth hereinabove.

When an acid thiamine compound or salt complex is administered, the compound or salt may or may not be chemically or enzymatically degraded in vivo to liberate dichloroacetate and thiamine per se. In any event, however, dichloroacetate and thiamine are provided in the biological system in an active form capable of performing their therapeutic function, i.e., amelioration of the metabolic disorder and reduction of the toxic effects of the dichloroacetate.

The invention is illustrated by the following non-limiting example.

EXAMPLE

Thirty-two male rats (285 G) received for 2 mos. Purina chow and either DCA (sodium dichloroacetate) (1.9 g/kg) in water or DCA in water plus ip injections of 600 μg $B_1$ 3×/wk. Each animal was examined weekly for signs of thiamine deficiency well-described in the literature for rats [Plaitakis et al., Ann. N.Y. Acad. Sci. 378:367 (1982)]; Hakim and Pappins, Ann. Neurol. 13:365 (1983)]. A numerical grading scale of 1 to 5 was used for each of seven separate clinical indices of thiamine deficiency. These values were needed to calculate individual and mean "severity index" [SI] of presumed deficiency at the end of two months. $B_1$ deficiency was also assessed by red cell transketolase (RCT) activity (mmol/min.). Blood samples were obtained periodically for determination of plasma DCA levels. After one month and again on the penultimate day of the study, a 24-hour urin sample was collected for measurement of oxalate. On the last day of the two-month study, the rats were sacrificed and blood was taken for examination of DCA levels. The results are set forth in Table 1.

TABLE 1

| Group | SI | RCT | DCA | OX |
|---|---|---|---|---|
| Control | 12 ± 4 | 143 ± 7 | — | 79 ± 6 |
| DCA | 39 ± 11 | 108 ± 6 | 291 ± 2 | 147 ± 12 |

TABLE 1-continued

| Group | SI | RCT | DCA | OX |
|---|---|---|---|---|
| DCA + B$_1$ | 23 ± 6 | 148 ± 8 | 282 ± 12 | 101 ± 12 |

DCA increased SI over 3-fold above control and decreased RCT 25%. Addition of B$_1$ reduced by 41% the SI seen with DCA alone and normalized RCT. Plasma DCA (μg/ml) was not significantly affected by B$_1$. After 2 mos., urinary OX (μg/ml) was 86% above control in DCA rats but only 28% above control DCA+B$_1$ rats.

I claim:

1. The chemical compound formed by the reaction between thiamine or a pharmaceutically active derivative thereof and a dichloroacetic acid.

2. A pharmaceutical composition in unit dosage form adapted for administration to a lower animal or human for the treatment of a metabolic disease comprising a therapeutically effective amount of (1) the compound of claim 1 or a salt of a pharmaceutically acceptable cation and dichloroacetic acid and (2) an amount of thiamine or a pharmaceutically active derivative thereof sufficient to reduce the toxicity to said lower animal or human of said compound or said salt of dichloroacetic acid.

3. The composition of claim 2 in combination with a pharmaceutically acceptable carrier.

4. The composition of claim 2 containing from about 10 to about 10,000 mg of said salt of dichloroacetic acid or said compound.

5. The composition of claim 2 wherein the mass ratio of the amount of thiamine or pharmaceutically active derivative thereof to the amount of salt of dichloroacetic acid or said compound is from about 0.00001:1 to about 10:1.

6. The composition of claim 5 wherein said mass ratio is from about 0.001:1 to about 0.2:1.

7. The composition of claim 2 wherein said cation is selected from the group consisting of alkali metals, alkaline earth metals, heavy metals and ammonium.

8. The composition of claim 7 wherein said salt of dichloroacetic acid is an alkali metal dichloroacetate.

9. The composition of claim 8 wherein salt of dichloroacetic acid is sodium dichloroacetate.

10. The composition of claim 2 adapted for the treatment of a metabolic disease selected from the group consisting of diabetes mellitus, hyperlipidemia and lactic acidosis.

11. The composition of claim 3 in pill, capsule or tablet form and adapted for oral administration to a lower animal or human.

12. The composition of claim 2 in lyophilized form.

13. The composition of claim 3 in a form adapted for transdermal or parenteral administration to a lower animal or human.

14. The composition of claim 2 in kit form comprising separately packaged therapeutically effective amounts of said dichloroacetic acid salt to said compound in a form adapted for administration to a lower animal or human and therapeutically effective amount of thiamine in a form adapted for administration to a lower animal or human.

15. A method for the treatment of a metabolic disease comprising administering to a lower animal or human in need thereof a therapeutically effective amount of the compound of claim 1 or a salt of a pharmaceutically acceptable cation and dichloroacetic acid and an amount of thiamine or a pharmaceutically active derivative thereof necessary to reduce the toxicity to said lower animal or human of said compound or said salt.

16. The method of claim 15 wherein the amount of said salt or compound administered to said lower animal or human animal is from about 1 to about 100 mg/kg.

17. The method of claim 16 wherein the amount of said salt or compound administered is from about 10 to about 50 mg/kg.

18. The method of claim 15 wherein the mass ratio of thiamine or pharmaceutically active derivative thereof to said salt or compound is from about 0.00001:1 to about 10:1.

19. The method of claim 18 wherein said mass ratio is from about 0.001:1 to about 0.2:1.

20. The method of claim 15 wherein said cation is selected from the group consisting of alkali metals, alkaline earth metals, heavy metals and ammonium.

21. The method of claim 20 wherein said salt of dichloroacetic acid is an alkali metal dichloroacetate.

22. The method of claim 21 wherein salt of dichloroacetic acid is sodium dichloroacetate.

23. The method of claim 15 adapted for the treatment of a metabolic disease selected from the group consisting of diabetes mellitus, hyperlipidemia and lactic acidosis.

24. The method of claim 15 wherein said compound or salt and thiamine or pharmaceutically active derivative thereof are administered orally in pill, capsule or tablet form.

25. The method of claim 15 wherein said compound or salt and thiamine or pharmaceutically active derivative thereof are administered parenterally.

26. The method of claim 15 including the step of combining said salt or compound with said thiamine or pharmaceutically active derivative thereof before administration.

27. The method of claim 15 wherein said compound or salt and said thiamine or pharmaceutically active derivative thereof are administered substantially simultaneously.

28. The method of claim 15 wherein said compound or salt and said thiamine or pharmaceutically active derivative thereof are administered sequentially.

29. The method of claim 15 wherein said compound or salt is administered prior to administration of said thiamine or pharmaceutically active derivative thereof.

30. The method of claim 15 wherein said thiamine or pharmaceutically active derivative thereof is administered prior to administration of said compound or salt.

* * * * *

UNITED STATES PATENT AND TRADEMARK OFFICE
CERTIFICATE OF CORRECTION

PATENT NO. : 4,558,050

DATED : December 10, 1985

INVENTOR(S) : Peter W. Stacpoole

It is certified that error appears in the above-identified patent and that said Letters Patent is hereby corrected as shown below:

Claim 14, line 3, please change "to" to "or".

Signed and Sealed this

Fourth Day of March 1986

[SEAL]

Attest:

DONALD J. QUIGG

Attesting Officer

Commissioner of Patents and Trademarks